United States Patent
Paulson

(10) Patent No.: US 9,144,513 B2
(45) Date of Patent: Sep. 29, 2015

(54) STYE CARE KIT AND METHOD

(76) Inventor: Suzanne Paulson, Temecula, CA (US)

( * ) Notice: Subject to any disclaimer, the term of this patent is extended or adjusted under 35 U.S.C. 154(b) by 921 days.

(21) Appl. No.: 12/622,424

(22) Filed: Nov. 19, 2009

(65) Prior Publication Data

US 2010/0125255 A1   May 20, 2010

Related U.S. Application Data

(60) Provisional application No. 61/116,168, filed on Nov. 19, 2008.

(51) Int. Cl.
    *A61M 35/00* (2006.01)
    *A61F 7/02* (2006.01)
    *A61F 7/00* (2006.01)

(52) U.S. Cl.
    CPC ........... *A61F 7/02* (2013.01); *A61F 2007/0004* (2013.01); *A61F 2007/026* (2013.01)

(58) Field of Classification Search
    CPC .......... A61F 13/12; A61F 9/00; A61F 13/00; A61F 2007/0004; A61F 2007/026
    USPC ............ 604/289–291, 294–296, 402; 602/41, 602/54, 57–59, 61, 74; 607/108, 109, 114
See application file for complete search history.

(56) References Cited

U.S. PATENT DOCUMENTS

| | | | | |
|---|---|---|---|---|
| 2,389,223 | A * | 11/1945 | Werner | 2/15 |
| 3,952,735 | A * | 4/1976 | Wirtschafter et al. | 602/74 |
| 4,243,041 | A * | 1/1981 | Paul | 607/109 |
| 5,769,806 | A * | 6/1998 | Radow | 602/41 |
| 6,090,060 | A * | 7/2000 | Radow | 602/74 |
| 2001/0039442 | A1* | 11/2001 | Gorge et al. | 607/109 |
| 2003/0056281 | A1* | 3/2003 | Hasegawa | 2/428 |
| 2006/0200052 | A1* | 9/2006 | Lin | 601/70 |
| 2014/0277303 | A1* | 9/2014 | Biser et al. | 607/104 |
| 2014/0330222 | A1* | 11/2014 | Bruder et al. | 604/290 |
| 2015/0047649 | A1* | 2/2015 | Paulson | 128/858 |

\* cited by examiner

*Primary Examiner* — Susan Su
(74) *Attorney, Agent, or Firm* — Donn K. Harms

(57) ABSTRACT

A stye treatment device for concurrent application of temperature and moisture to a stye. The device features a moisture component positioned in a central cavity formed in a sealing edge extending from the rear surface of an eyecup. A temperature component is positioned in the cavity rearward of the moisture component in a position to contact a stye when the device is biased by a strap to the face of the user. The device, when worn by the user, may impart either heat or cold temperature treatments and humidity or moisture treatment concurrently. Excessive pressure against the user's stye and eye is prevented by forming the moisture component of material adapted to collapse should the temperature component contact the face of the user under too much pressure which might otherwise cause pain.

7 Claims, 1 Drawing Sheet

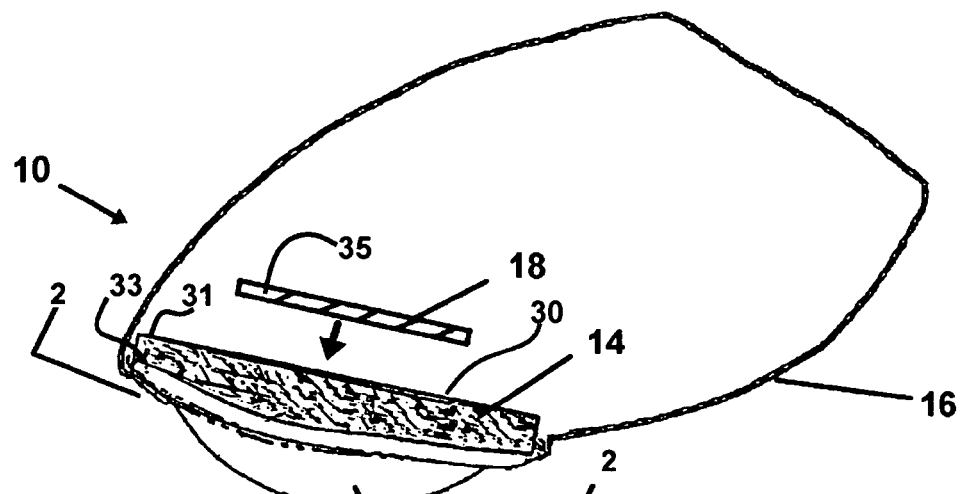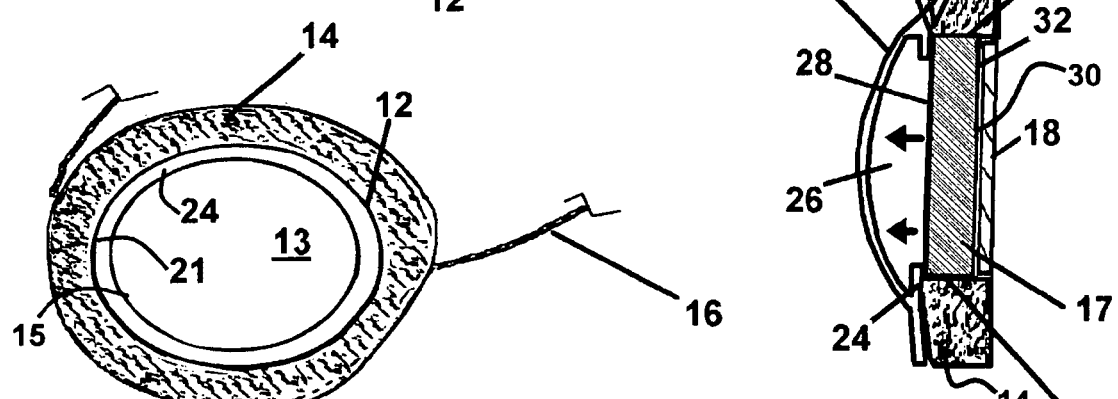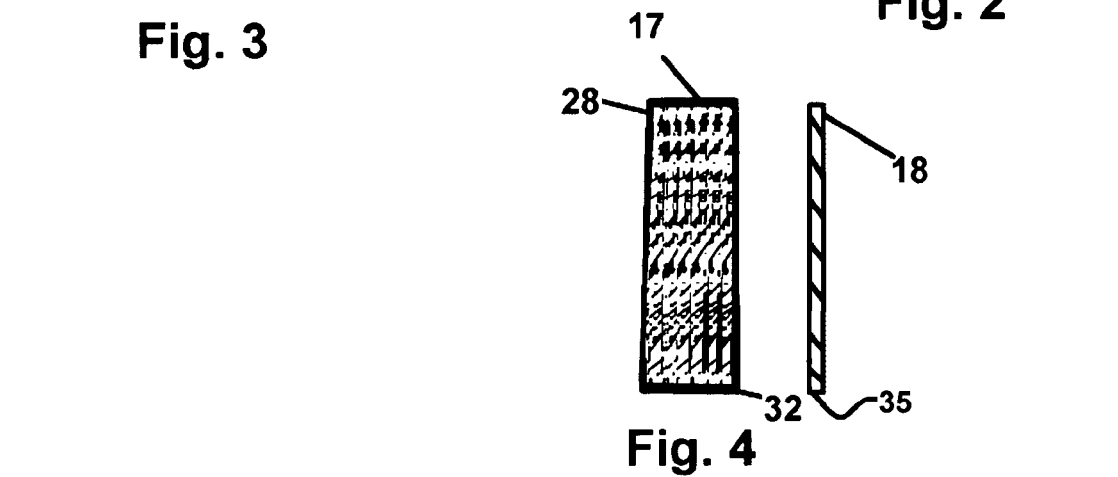

STYE CARE KIT AND METHOD

This application claims priority to U.S. Provisional Patent Application No. 61/116,168 filed on Nov. 19, 2008 and incorporated herein in its entirety by reference. This invention relates generally to an apparatus, system and method for treating styes which occur in the eyes of humans and animals. More particularly the device relates to a wearable treatment for providing heating, cooling, and moisturizing to a stye which during such treatment allows the user to maintain their regular schedule of work and relaxation.

FIELD OF THE INVENTION

Background of the Invention

A stye or hordeolum is an infection of the sebaceous glands at the base of the eyelashes. While styes generally produce no lasting damage, they can be annoying quite painful. Much like acne, styes can make the patient self-conscious about their appearance, and should they become too swollen, can interfere with vision.

While the infections from most styes will drain on their own accord over time, this process can be accelerated by the application of a hot or warm compress to the affected eye. It may also be accelerated by removal of the offending eyelash and by a flushing out of the eye. With such treatments, styes typically resolve within one week or slightly longer. Styes may also cause a bruised feeling around the eye which can be treated through the application of a warm cloth.

Medical professionals generally prescribe a hot compress as the best way to treat the stye. The warmth communicated to the eye, combined with dampness, encourages the stye to drain. Alternatively, a cold compress combined with moisture will generally discourage or prevent more swelling of the eyelid.

Currently, treatment with a warm compress involves making the warm compress by placing hot water on a wash cloth, or employing a warm hard-boiled egg, or using a baked potato wrapped in a moist paper towel or washcloth. The application of the compress and communication of heat to the eye and stye increases the blood flow to the affected area and encourages the patient's white blood cells to attack the infection causing the stye. Should a cold compress be desired, it is generally provided using cold water or ice or cold gel packs and touching the compress to the eye.

However, a dilemma faces a stye patient. Placing pressure on the stye can be quite painful. To effectively communicate heat or cold from a compress to the stye area, and to transmit moisture, the wash cloth, or egg, ice cube, or other device providing a means for temperature differential from body temperature, must be pressed into the eye and stye.

As a consequence of the discomfort of pressure on the eye, some patients avoid such treatment altogether which results in a prolonging of their illness due to their aversion to the pain of the compress. Additionally, treatment is also avoided by patients due to the inconvenience since to apply heat to the stye they must continually heat water and wash cloths, or heat retention devices, and apply them to their eye in a delicate manner. This is both time consuming, and inconvenient.

Still further, many such patients miss work due to the fact that fluids will exit their eye during an infection. Staying away from co-workers due to fears of infection of other workers and the embarrassment of having to be viewed with an infection in their eye by co workers, is a major reason stye sufferers take sick days off work.

As such, there is an unmet need, for a stye treatment which provides a means to impart a temperature differential from the body temperature of a patient suffering a stye. Such a temperature communication to the affected area should be providable in both hot and cold compresses. Such a device should best be able to concurrently provide a communication of moisture to the affected eye being treated. Additionally, such a device should provide this means to impart heat or cold to the affected eye without the need to heat or cool water and soak cloths for hand compresses to be used upon the patient's eye. Further, such a device and method should eliminate the inconvenience and mess associated with providing a hot or cold stye compress.

Particularly preferred in such a device and method is the ability to provide a means to impart the heat source, or cold compress source in contact against the stye. In doing so, the device and method must also concurrently provide a means to relieve any excess or over-pressure against the eye and stye of the patient to minimize pain caused by pressured contact and the resulting aversion to employ it. Still further, in addition to controlled compressive contact treatment, such a device should concurrently provide the patient's eye with a temperature treatment such as hot or cold compresses, at limited contact pressure and with moisture but without the conventional mess, dripping and inconvenience of conventional hot cloths.

SUMMARY OF THE INVENTION

Generally speaking, the present invention is directed toward an apparatus, system and method for treating styes which occur in the eyes of patients suffering such an illness. The device is constructed to appear substantially as an eye patch and is adapted at a perimeter edge for a sealed engagement with the eye socket surrounding the eye. Employing this sealed engagement, the wall of the cup-like eye patch forms a chamber between the device and the surfaces of the eye and surrounding facial structure. This chamber thereby provides a means to maintain moisture and high humidity in the chamber in a communicating fashion in front of the eye of the patient.

As noted, the disclosed device employs an eye cup that is formed of substantially water proof and non air permeable material. For comfort over long durations of use, the eye cup material is formed of resilient material with a soft and pliable edge portion at least. The perimeter edge portion is best contoured to encircle the orbital bones of the eye sockets.

The soft contact of the sealing edge of the cup provides a means to thereby create a custom and comfortable fit around the area of the eye socket. The seal between the edge and the eye socket surface also provides an effective seal to isolate the chamber formed over the eye of a patient suffering from a stye from the outside world.

A flexible strap engaged to opposite sides of the cup, provides a gentle means to bias the cup toward the face of the user and concurrently compress its seal against the face around the eye to maintain a seal and form an internal cavity in front of the eye. Other means to maintain the seal and soft edge in a contact with the face around the eye may be employed, however currently an elastic or other band provides an effective means.

The cavity formed by the aperture extending into a soft sealing edge engaged to the cup, and a central portion of the inside wall of the cup itself, and the face and eye of the user, has a diameter larger than the eye of the user. This cavity, so formed, extends toward the interior surface of the cup axially a distance in front of the patient's eye when the device is in an as-worn position as a patch.

Further, in a particularly preferred mode of the device, interior sidewalls of the soft sealing edge of each eyecup are adapted in diameter to provide means to compressibly and frictionally engage with removably engageable moisture pads. The moisture pads in one mode of removable engagement, frictionally engage the sidewall forming the inside surface of the soft sealing edge extending from the eyecup. The frictional engagement is provided by forming the pads of resilient material equal to, or slightly larger than, the diameter across the cavity formed by the sidewall of the cavity formed in the soft sealing edge material. Thus, when formed of elastic material, such as foam, they will naturally expand when compressed and frictionally engage against the sidewall to hold themselves in the cavity during use.

A ledge may also be formed on the inside surface of the sealing material extending around the perimeter of the eye cup. This ledge may be adapted in size to engage with a small portion of the removable moisture pads adjacent to their circumferential edge. When pushed into the cavity formed by the sidewall of the sealing material, the moisture pad will bottom out on the ledge leaving a centrally disposed empty space between the leading side surface of the moisture pad and the interior surface of the cup. This empty space area provided in the preferred mode forms an expansion chamber which provides a means for deflection of the soft moisture pad into the empty space and toward the eye cup, when pressure from the user's eye, communicated to the opposite side of the soft moisture pad exceeds a very small level. This deflection provides a means to prevent excess pressure on the patient's eye and stye during use and may be adjusted by adjusting the hardness or deflecting qualities of the material forming the moisture pad such as sponge or open cell foam material.

This deflection into the formed expansion chamber, along with the natural compression characteristics of the foam material, provides a means to ensure that only a very slight pressure is exerted to a heating or cooling component and against the patient's eye. The heating or cooling component, engaged within a rearward cavity formed by the sidewall of the foam type sealing edge material, will deflect toward the eye cup if excess pressure is applied over that which deflects the foam material into the empty space.

The heating component, or similar cooling component, so engaged in the rearward cavity is positioned to contact with the eyelid and the stye and provide temperature related treatment to the area. The moisture pad formed of absorbent material, such as open cell foam, provides continuous moisture to the rearward cavity since the sealing edge maintains the area in front of the eye as a sealed chamber.

Means to ensure that pressure of the heating or cooling element against the eye is minimal or very slight is provided by both the compression or compacting of the foam forming the moisture pad and the deflection of the moisture pad toward the eye cup interior wall.

The heating element may be a conventional chemically activated gel type heating component inside a soft plastic casing. Once initiated to heat, and engaged in the rearward cavity, the user places the eyecup against their face to position the heating element lightly biased against the eyelid by the compaction of the sealing edge which is also formed of a foam material. Cooling elements exist in a similar fashion wherein chemically induced cold may be obtained or a gel pack may be cooled in the freezer. The elastic strap, pulling on both sides of the eyecup, holds the sealing edge against the face and causes the side surface or the cooling or heating component to contact with the eyelid of the user. The heating or cooling elements may also be simple packets filled with material or liquid adapted to chill or heat when subjected to the same in warm water, a microwave oven, or a freezer.

On contact, the foam forming the moisture pad will slightly compress or deflect from the pressure of the heating or cooling component on the eyelid being communicated to the moisture pad. If a force from that pressure exceeds that which is very slight, and the compaction of the moisture pad cannot absorb it, the moisture pad itself will deflect into the deformation cavity formed between the opposite side of the moisture pad and the interior surface of the eyecup up to the ledge.

It is thus an object of this invention to provide a system for treating styes that allows the user to concurrently apply heat or cold to the stye along with moisture to the stye and area around it.

It is further an object to provide such a device that may be worn while working or relaxing to treat the stye.

It is yet a further object to provide such a temperature and moisture stye treatment which also protects the user from the pain caused by excess pressure on the stye by providing two means to minimize or eliminate excess pressure.

Further, it should be noted that the invention accordingly comprises the features of construction, combination of elements, and arrangement of parts which will be exemplified by the constructions hereinafter set forth, and the scope of the invention will be indicated in the claims. However, those skilled in the art will realize that different components and arrangements may be employed to yield the invention and all such modifications as would occur to those skilled in the art are considered within the scope of this invention.

BRIEF DESCRIPTION OF THE DRAWING FIGURES

In the drawing figures, which are not to scale, and which are merely illustrative and wherein like reference characters denote similar elements throughout the several views:

FIG. 1 is a side perspective view of the device for concurrently providing moisture and heat or cold under slight pressure to a stye.

FIG. 2 is a slice through FIG. 1 along line 2 showing the deflection chamber formed by the ledge engaging the sidewall of the moisture pad when inserted within the sidewall of the sealing edge material.

FIG. 3 shows a rear view of the device and the cavity formed by the sidewall of the sealing edge material which is adapted to frictionally engage the moisture pad.

FIG. 4 shows a side view of the moisture pad formed of foam which compresses and then deflects under pressure and of the temperature component from force against the patient's face.

DETAILED DESCRIPTION OF THE PREFERRED EMBODIMENTS

Referring now to the drawings in FIGS. 1-4 wherein similar parts are identified by like reference numerals, there is seen in FIG. 1, a perspective view of the device 10 showing the eyecup 12 having a soft foam-like sealing edge 14 engaged around a circumference of the rearward side 13 of the eye cup 12.

A strap 16 made from elastic material or other means for biased positioning against the user's face, holds the sealing edge 14 material biased against the user's face when the device is in the as-worn position engaged over one eye of a patient. The bias of the elastic strap 16 pulling on the eye cup 12 sandwiches the sealing edge 14 between the face of the user and eye cup 12.

A moisture pad 17 is provided and adapted to frictionally engaged with a cavity 15 defined by the surface of an interior sidewall 21 of the sealing edge 14 extending from a first end 31 of the sealing edge 14, to a second end 33 thereof engaged with the eye cup 12. As noted the moisture pad 17 is preferably soft and compressible being formed of open cell foam or similar material which will hold hot water or cold water when soaked therein. In use, the moisture pad 17 is placed in biased engagement with the sidewall 21 forming the axial cavity 15.

A ledge 24 may be formed on the rearward side 13 of the eye cup 12 or the second end 33 of the sealing edge 14 and acts to stop the insertion of the moisture pad 17 and to define a deflection cavity 26 area defined by the depicted curved interior wall surface of the rearward side 13 of the eye cup 12, the edge of the ledge 24, and the leading side surface 28 of the moisture pad 17. As clearly depicted in FIG. 2, the eye cup 12 is curved in a central portion in a curve which extends the rearward side 13 an increased distance away from an opposing central portion of the leading surface 28 of the moisture pad 17, than the distance from edge portions of the moisture pad 17. As noted, this deflection cavity 26 provides a second means to reduce excess pressure by allowing deflection of the moisture pad 17 therein so that excess pressure is not imparted to the stye by the bias of the elastic strap 16 and any developed compression of the sealing edge material. A first means to limit pressure on the stye or eye of the patient by the heating or cooling temperature element 18 may be provided by a determined compression ability of the foam material itself forming the moisture pad 17. This compressive ability may be adjusted by adjusting the material' forming the moisture pad 17 to be softer or harder and thus more or less resistant to compression at a force above a predefined level determined to help communicate heat or cold to the stye but prevent pain from over-pressure.

The temperature element 18 provided may be chemically activated or formed with material which may be simply heated in hot water for heat and frozen or chilled to communicate cold to the stye. The temperature element 18 may have a perimeter 35 adapted to engage within the sidewall 21 of the sealing edge 14 in a mounting cavity 30 defined by a rear wall surface 32 of the moisture pad 17 and the sidewall 21 extending a distance between rear wall surface 32 and the first end 31 of the sealing edge 14. A determined thickness of the temperature element 18 may be varied if more or less pressure is desired on the stye taking into consideration the deflection into the deflection cavity 26 and the compressive nature of the foam or other water-holding material forming the moisture pad 17.

In a method of use, the user would soak the moisture pad 17 in a warm or cold solution such as water and insert it within the sidewall 21 until it frictionally engages or until it bottoms out on the ledge, if provided, within the formed mounting cavity. Next the temperature element 18, if desired to apply heat, would be activated chemically or heated in hot water or other fluid. If the temperature element 18 is to communicate cold, it could be activated chemically or removed from a cold source such as the freezer. The temperature element 18 is inserted in the mounting cavity 30 and then the assembled device 10 is placed on the face of the user and surrounding the eye to be treated. The elastic strap 16 or other biasing means is then engaged around the head holding the device 10 in place for the duration of treatment with heat, cold, and/or moisture concurrently.

Those skilled in the art will no doubt realize that two cups 12 engaged by a bridge may be employed to treat two eyes at the same time using individual configurations for heat, cold, and moisture noted above. All such configurations are considered within the scope of this application.

The present invention thus overcomes various shortcomings of the currently available treatments for styes by concurrently providing heat at a very slight pressure and moisture in a compact and conveniently worn device. Further, over-pressure and pain to the user is prevented by the compressive material for the moisture pad 17 and/or deflection.

Although the invention has been described with respect to particular embodiments thereof, it should be realized that various changes and modifications may be made therein without departing from the spirit and scope of the invention. While the invention as shown in the drawings and described in detail herein discloses arrangements of elements of particular construction and configuration for illustrating preferred embodiments of structure and method of operation of the present invention, it is to be understood, however, that elements of different construction and configuration and other arrangements thereof, other than those illustrated and described, may be employed in accordance with the spirit of this invention. Any and all such changes, alternations and modifications as would occur to those skilled in the art are considered to be within the scope of this invention as broadly defined in the appended claims.

Further, the purpose of the attached abstract is to enable the U.S. Patent and Trademark Office and the public generally, especially scientists, engineers and practitioners in the art who are not familiar with patent or legal terms or phraseology to determine quickly, from a cursory inspection, the nature and essence of the technical disclosure of the application. The abstract is neither intended to define the invention of the application, which is measured by the claims, nor is it intended to be limiting as to the scope of the invention in any way.

What is claimed is:

1. A stye treatment apparatus comprising:
an eyecup, said eyecup having a soft, pliable sealing edge projecting from a first end to a second end thereof engaged with a circumference of said eyecup at a rearward side of said eyecup;
a cavity, said cavity surrounded by said sealing edge and defined by a sidewall of said sealing edge extending between said first end and second end thereof;
a moisture pad comprises a body having a leading side opposite a rear wall and having a side surface communicating therebetween, said moisture pad sized for removable engagement within said cavity;
said body of said moisture pad formed of material capable of absorbing a hot or cold liquid;
a temperature component, said temperature component having a perimeter adapted for removable positioning within a mounting cavity defined by said rear wall surface of said moisture pad in said removable engagement and said sidewall of said sealing edge between said first end of said sealing edge and said rear wall surface;
said temperature component formed of material adapted to store heat or cold and communicate said heat or cold to an exterior surface thereof;
said first end of said sealing edge adapted for contact with facial skin surrounding an eye of a user in an as-worn position on the face of said user;
means to impart a biasing force to bias said first end of said sealing edge to said as-worn position; and
said exterior surface of said temperature component in a positioning within said mounting cavity is adapted for direct contact with portions of said eye afflicted with a stye when said sealing edge is in said as-worn position, whereby heat or cold from said temperature component may be communicated directly to said stye, and moisture from said moisture pad communicates humidity to said mounting cavity which is positioned to surround said stye.

2. The stye treatment apparatus of claim 1 additionally comprising:
a deflection cavity defined by the an area between said rearward wall of the eye cup and said leading side surface of said moisture pad while in said removable engagement; and
a portion of said moisture pad deflectable into said deflection cavity should said biasing force exceed a determined maximum.

3. The stye treatment apparatus of claim 2 additionally comprising:
a ledge positioned adjacent said second end of said sealing edge; and
said ledge forming a contact for an edge of said leading side of said moisture pad when in said removable engagement with said cavity to form a stop at said second end of said sealing edge; and
said eye cup being curved in a central portion thereof, said curve positioning a central portion of said rearward side of said eye cup a greater distance from an opposing central portion of said leading surface than from said edge of said leading side in contact with said ledge.

4. The stye treatment apparatus of claim 3 wherein the temperature component may be either chemically activated or formed with a material which may be heated in hot water for heat or frozen or chilled to communicate cold to the stye.

5. The stye treatment apparatus of claim 3 wherein said direct contact of said temperature component with portions of said eye afflicted with a stye, provided by said positioning of said temperature component within said mounting cavity, is a direct contact with portions of said eye afflicted with a stye while said sealing edge is in said as-used position.

6. The stye treatment apparatus of claim 1 additionally comprising:
a ledge positioned adjacent said second end of said sealing edge; and
said ledge forming a contact for said leading side of said moisture pad when in said removable engagement with said cavity to form a stop at said second end of said sealing edge.

7. The stye treatment apparatus of claim 1 wherein said direct contact of said temperature component with portions of said eye afflicted with a stye, provided by said positioning of said temperature component within said mounting cavity, is a direct contact with portions of said eye afflicted with a stye while said sealing edge is in said as-used position.

* * * * *